United States Patent
Lauf et al.

(10) Patent No.: US 12,064,153 B2
(45) Date of Patent: Aug. 20, 2024

(54) LATERAL SPINE PLATE WITH SET SCREW LOCKING OF BONE SCREWS

(71) Applicant: Life Spine, Inc., Huntley, IL (US)

(72) Inventors: Garrett D. Lauf, Elgin, IL (US); Richard M. Mueller, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 200 days.

(21) Appl. No.: 17/113,883

(22) Filed: Dec. 7, 2020

(65) Prior Publication Data

US 2021/0085379 A1 Mar. 25, 2021

Related U.S. Application Data

(63) Continuation of application No. 15/438,569, filed on Feb. 21, 2017, now Pat. No. 10,856,919.

(Continued)

(51) Int. Cl.
*A61B 17/80* (2006.01)
*A61B 17/70* (2006.01)
*A61B 17/86* (2006.01)

(52) U.S. Cl.
CPC ...... *A61B 17/8057* (2013.01); *A61B 17/7059* (2013.01); *A61B 17/8042* (2013.01); *A61B 17/8061* (2013.01); *A61B 17/8605* (2013.01)

(58) Field of Classification Search
CPC ............ A61B 17/8042; A61B 17/8047; A61B 17/8033; A61B 17/8038; A61B 17/8052; A61B 17/8057; A61B 17/8605
See application file for complete search history.

(56) References Cited

U.S. PATENT DOCUMENTS 8,105,367 B2   1/2012 Austin et al.
8,945,193 B2   2/2015 Kirschman
(Continued)

FOREIGN PATENT DOCUMENTS

DE   10 2005 042 766 A1   8/2009
EP        0 938 872 A1   9/1999
(Continued)

OTHER PUBLICATIONS

English Machine Translation of EP-0988833. (Year: 2022).*
International Search Report on PCT/US2017/018775, May 18, 2017, 5 pages.

*Primary Examiner* — Amy R Sipp
(74) *Attorney, Agent, or Firm* — Foley & Lardner LLP

(57) ABSTRACT

A lateral spine implant has a plate, configured bone screws, and configured setscrews providing locking of bone screw movement. The plate has at least two identically configured bone screw bores, each one with a spherical seat at a bottom opening, and threads around the inner circumference of a top opening. Each setscrew has a cylindrical body with external threads that mate with inner threads of the bone screw bore in order to affix the setscrew to the plate. A threaded spherical pocket is provided in a bottom of the setscrew body which conjoins with the spherical bone screw head to secure the setscrew with the bone screw head, fixing bone screw orientation/angulation. The bone screw head has a formation or formations about at least a portion of its exterior circumference that cooperate with the threads of the spherical pocket of the plate in order to fix bone screw orientation/angulation.

15 Claims, 5 Drawing Sheets

Related U.S. Application Data

(60) Provisional application No. 62/298,157, filed on Feb. 22, 2016.

(56) References Cited

U.S. PATENT DOCUMENTS

| | | | | |
|---|---|---|---|---|
| 2004/0116929 | A1* | 6/2004 | Barker | A61B 17/7037 606/907 |
| 2006/0271047 | A1* | 11/2006 | Jackson | A61B 17/7037 606/270 |
| 2010/0004691 | A1* | 1/2010 | Amato | A61B 17/808 606/280 |
| 2010/0241175 | A1 | 9/2010 | Walker et al. | |
| 2011/0137314 | A1* | 6/2011 | Kuster | A61B 17/74 606/281 |
| 2011/0166573 | A1 | 7/2011 | Wenk et al. | |
| 2011/0313466 | A1* | 12/2011 | Butler | A61B 17/8695 606/301 |
| 2012/0029576 | A1* | 2/2012 | Cunliffe | A61B 17/8085 606/289 |
| 2012/0071933 | A1* | 3/2012 | DeRidder | A61B 17/7059 606/281 |
| 2013/0345813 | A1* | 12/2013 | Frank | A61B 17/8023 623/17.16 |
| 2014/0018862 | A1 | 1/2014 | Koay et al. | |
| 2015/0112393 | A1* | 4/2015 | Garber | A61B 17/7058 606/279 |
| 2017/0065312 | A1 | 3/2017 | Lauf et al. | |

FOREIGN PATENT DOCUMENTS

| | | |
|---|---|---|
| EP | 0 988 833 A2 | 3/2000 |
| EP | 0988833 A2 * | 3/2000 ......... A61B 17/8042 |

* cited by examiner

LATERAL SPINE PLATE WITH SET SCREW LOCKING OF BONE SCREWS

CROSS-REFERENCE TO RELATED PATENT APPLICATIONS

This application is a continuation of U.S. application Ser. No. 15/438,569, filed Feb. 21, 2017, which claims the benefit of and priority to U.S. Provisional Application No. 62/298,157, filed Feb. 22, 2016, both of which are hereby incorporated herein by reference in their entireties.

BACKGROUND

The present invention relates to orthopedic implants such as plates and screws for the spine and, more particularly to lateral spine plate implants having bone screw locking features.

People contend with spine issues as a result of age, disease, trauma, and congenital and acquired complications and conditions. While some of these issues can be alleviated without surgery, other issues respond better to surgery. In some cases, surgery may include installing an orthopedic implant.

One type of orthopedic implant for the spine is a plate or plate construct along with bone screws for attaching the plate/plate construct to vertebrae of the spine. Various spine plates have been developed over the years for general, particular and specific use. There are spine plates for anterior attachment to the spine, spine plates for posterior attachment to the spine, and spine plates for lateral attachment to the spine. Spine plates are attached to vertebrae by bone screws.

With all types of spine plates including laterally attached (lateral) spine plates, it is important to stop or at least limit rotation of the bone screws once installed. Rotation of the bone screws after attachment of the spine plate compromises the integrity of the spine plate and its ability to perform its intended function of preventing horizontal movement of the vertebral bodies.

While various lateral spine plates have been designed over the years to combat bone screw rotation, they are deficient in many respects. It is therefore an object of the present invention to provide a lateral spine plate that overcomes the deficiencies of the prior art.

SUMMARY

A lateral spine plate implant is characterized by a lateral spine plate that utilizes configured setscrews, configured bone screw bores, and configured bone screws to inhibit rotation and/or fix orientation of a bone screw received in the lateral spine plate.

The lateral spine plate has at least two at least similar, but preferably, although not necessarily, identical, configured bone screw bores, each one with a rounded seat that preferably, but not necessarily, has circumferential threads at a bottom opening of the bone screw bore/rounded seat, and circumferential threads around the inner periphery of a top opening of the bone screw bore. Each one of the configured bone screw bores is designed to cooperate with a configured head of a bone screw to allow up to 360° angulation and fixation of the bone screw about the bone screw bore.

Each setscrew has a cylindrical body with threads around its external circumference that are configured to mate with the circumferential threads of the inner periphery of the top opening of the bone screw bore in order to affix the setscrew to the lateral spine plate. Each setscrew further has a configured socket in a top of the setscrew body, and a domed or spherical pocket in a bottom of the setscrew body. A bottom of the socket and a top of the pocket are preferably, but not necessarily, in communication with each other. Threads are provided around the inner circumference of the domed pocket which cooperate with the bone screw head to secure the setscrew with the bone screw head in order to fix bone screw orientation/angulation.

The bone screw has a dome shaped head and a threaded shank. The head has a configured socket in a top thereof, and a formation or formations about at least a portion of its exterior circumference. The formation(s) of the bone screw head cooperate with the threads of the inner circumference of the domed pocket in order to fix bone screw orientation/angulation. In one form, the formation(s) comprise serrations about its exterior surface. In another form, the formation(s) comprise knurling around its exterior surface. In yet another form, the formation(s) comprise one or more helical cutouts about its exterior surface. In a still further form, the formation(s) comprise threading. All of these formations or features provide a greater resistance to rotation once the bone screw head is fully seated in the setscrew pocket. The configurations (formation(s) or features) of the bone screw head and the setscrew pocket allow the two components to seize/bind with one another when the setscrew is threaded down onto the top of the bone screw head.

The lateral spine plate has a general curve to its body with a bone screw bore on either end, each bone screw bore preferably, but not necessarily, having a raised rim. A threaded hole in the mid portion of the lateral spine plate body accepts any necessary instrument(s) for insertion, placement, adjustment and holding of the lateral spine plate during installation/implantation.

For installation/implantation, the lateral spine plate is placed on top of the vertebral bodies lateral or anterolateral. Bone screws are then placed into the bone screw bores until they are fully seated in the seat. A setscrew is threaded into each bone screw bore and on the top of the bone screw head. Each setscrew provides compression to the bone screws/bone screw heads in order to engage the serrations/knurling/threading/helical cutout formation(s) of the bone screw head into the bone screw pocket of the plate to set bone screw orientation. This inhibits rotation of the bone screws relative to the plate, thus preventing any horizontal movement of the vertebral bodies.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate forms of the present invention, wherein.

DETAILED DESCRIPTION

Figure 1:
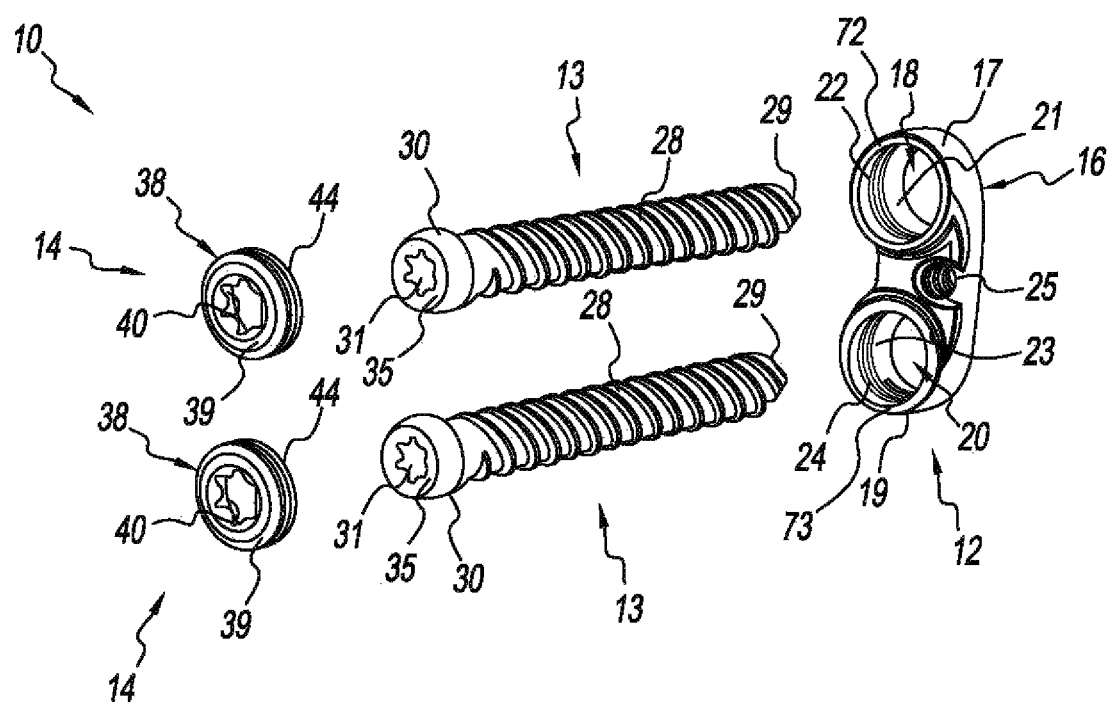
FIG. 1 is an exploded isometric view of the components of the present lateral spine plate implant.
Figure 2:
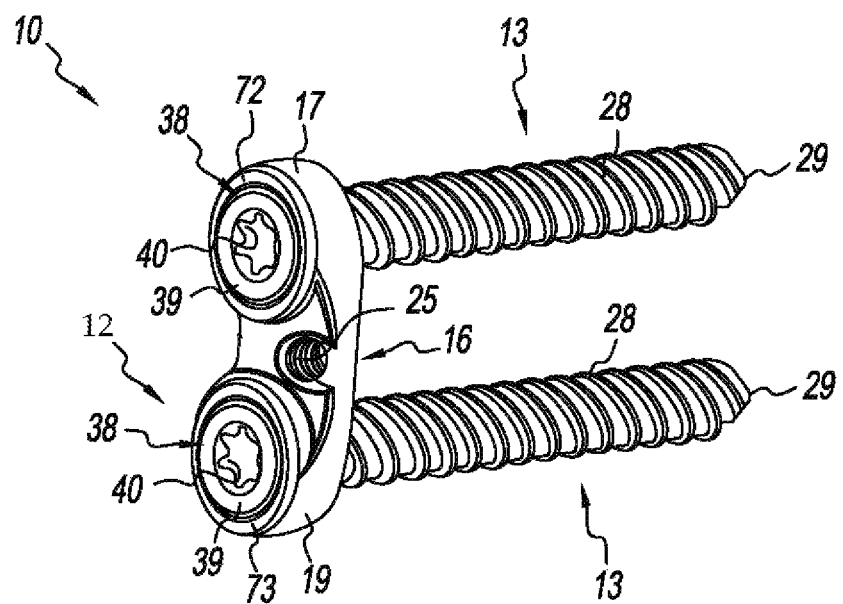
FIG. 2 is an isometric view of the lateral spine plate implant of FIG. 1, assembled.

Referring to FIGS. 1 and 2, an exemplary form of a lateral spine plate implant, generally designated 10, is shown fashioned in accordance with the present principles, with FIG. 1 depicting components of the lateral spine plate implant 10 in an exploded view, and FIG. 2 depicting the components of the lateral spine plate implant 10 in an assembled view. The lateral spine plate implant 10 is made from a biocompatible material such as, but not limited to, titanium, stainless steel, an alloy of titanium or steel, or other. The lateral spine plate implant 10 is characterized by a spine plate 12, two preferably, but not necessarily, identical bone screws 13, and two preferably, but not necessarily, identical setscrews 14. The lateral spine plate implant 10 is for any portion of the spine. Lateral spine plates of more than two bone screw bores may also be fashioned in accordance with the present principles.

The spine plate 12 is configured for lateral attachment to adjacent vertebrae. The spine plate 12 is characterized by a body 16 having a first boss 17 on one end of the body 16, and a second boss 19 on another end of the body 16, the nomenclature first and second being arbitrary here and throughout. The first boss 17 has a first bore 18 defining an upper opening area and a lower opening area. A first seat 21 is defined at the lower opening area of the first bore 18 by an annular, radially inwardly angled lower wall designed for reception of a bone screw and, particularly, the head of a bone screw, the radially angled lower wall defining the first seat at the bottom opening of the bone screw bore 18. The second boss 19 has a second bore 20 defining an upper opening area and a lower opening area. A second seat 23 is defined at the lower opening area of the second bore 20 by an annular, radially inwardly angled lower wall designed for reception of a bone screw and, particularly, the head of a bone screw, the radially angled lower wall defining the second seat at the bottom opening of the bone screw bore 20.

The upper opening area of the first screw bore 18 has threads or threading 22 around its inner circumferential surface or wall. The upper opening area of the second screw bore 20 also has threads or threading 24 about its inner circumferential surface or wall. The inner threads of the upper opening areas of the first and second bores 18, 20 are sized to receive outer threads 44 of a setscrew 14. The inner surface of the first seat or lower opening area 21 of the first bore 18 of the plate 12 shown in FIGS. 1-2 is generally smooth, but may be textured, configured, or otherwise non-smooth, if desired. The inner surface of the second seat or lower opening area 23 of the second bore 20 of the plate shown in FIGS. 1-2 is generally smooth, but may be textured, configured, or otherwise non-smooth, if desired. As an example, the inner surface or wall of the first and second seats or lower opening areas 21, 23 of the first and second bores 18, 20 of the plate 12a of FIG. 3, has threads 82, 84 around its circumference. Other formations may be used.

The plate body 16 has a general arch or curvature with a threaded bore 25 in a mid-section or portion of the plate body 16 to accept necessary tools and/or instruments for insertion, placement and manipulation of the plate during surgical installation/implantation. Other configurations may be used. The bone screw bores 18, 20 has a rim 72, 73 that is preferably, but not necessarily, raised relative to other plate portions as shown. The openings of the bone screw bores may be rimless or flush.

Each bone screw 13 is characterized by a rounded, spherical, or dome-shaped head 30 having a socket 31 in a top or upper surface 35 thereof. The socket 31 is configured in a star or hexagonal pattern for receipt of a like instrument or tool (not shown) for driving/installing the bone screw 13. Other configurations may be used and are contemplated. The bone screw 13 has a shank or shaft 28 with external threads/threading configured to drive into (be received by) a vertebral body (vertebra). The shank 28 terminates in a preferably, but not necessarily, pointed distal tip 29.

The shape of the head 30 defines an upper area or circumference 81, and a lower area or circumference 83. At least a portion of the outer circumference of the head 30 is preferably, but not necessarily, configured with one or more features or formations that aid in limiting, inhibiting and/or preventing rotation of the bone screw 13 relative to the spine plate 12 once the bone screw 13 has been installed. The features and/or formations do not need to extend the entire circumferential area of the head 30. Any such features and/or formations may extend about one or more portions or areas of one or more portions or areas of the circumference. Other patterns or areas may be used as desired.

Figure 4:
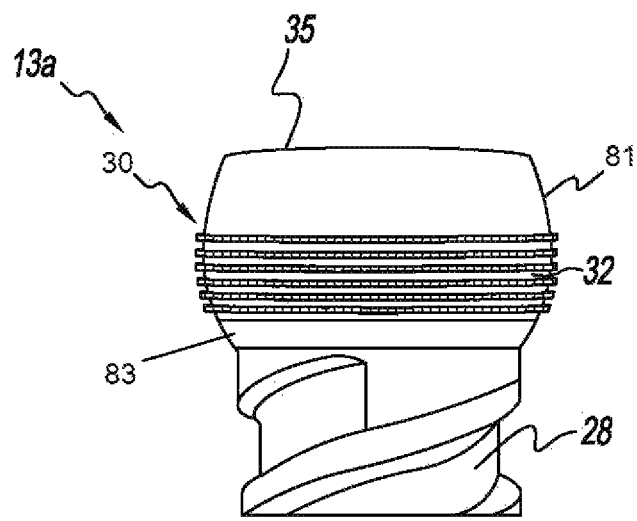
FIG. 4 is an enlarged side view of the head and partial shank of one form of the bone screw of the present lateral spine plate implant.

FIG. 4 depicts one type of anti-rotation feature/formation(s)/configuration 13a for the bone screw head 30. The head 30 of the bone screw 13a has serrations or the like 32 about at least a portion of its peripheral surface. It should be appreciated that the number, size and/or spacing of the serrations 32 may be changed as desired. The formation(s) may also aid in fixing bone screw angulation and/or orientation.

Figure 5:
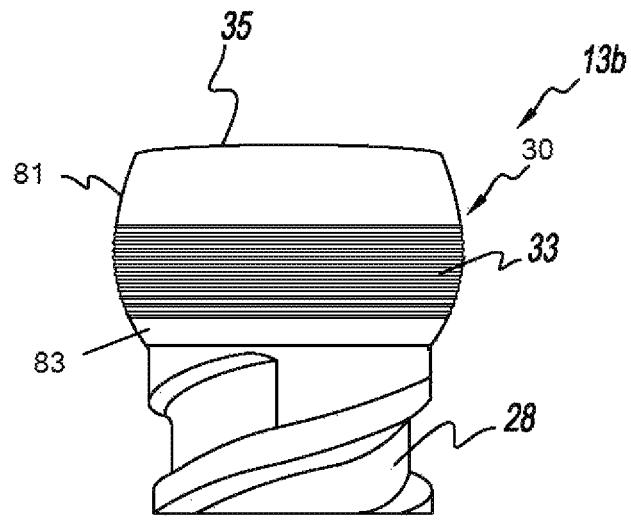
FIG. 5 is an enlarged side view of the head and partial shank of another form of the bone screw of the present lateral spine plate implant.

FIG. 5 depicts another type of anti-rotation feature/formation(s)/configuration 13b for the bone screw head 30. The head 30 of the bone screw 13b has knurling 33 about at least a portion of its peripheral surface. It should be appreciated that the number, size and/or spacing of the knurling 33 may be changed as desired. The formation(s) may also aid in fixing bone screw angulation and/or orientation.

Figure 6:
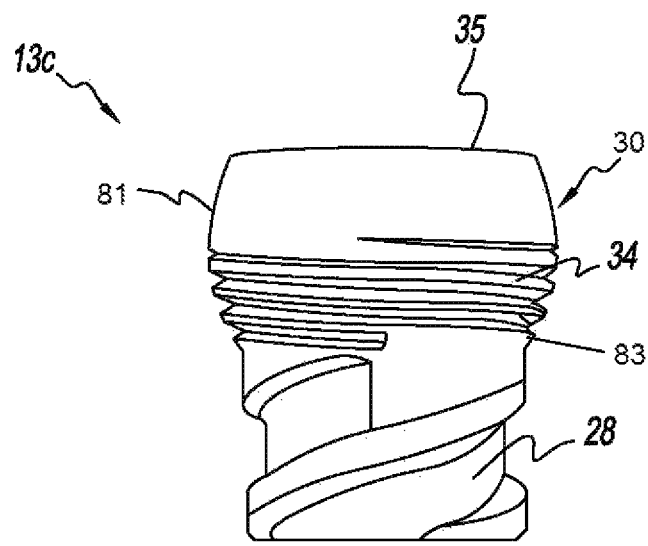
FIG. 6 is an enlarged side view of the head and partial shank of another form of the bone screw of the present lateral spine plate implant.

FIG. 6 depicts another type of anti-rotation feature/formation(s)/configuration 13c for the bone screw head 30. The head 30 of the bone screw 13c has a helical cutout 34 about at least a portion of its peripheral surface. It should be appreciated that the number, size and/or spacing of the helical cutout 34 may be changed as desired. Other types of anti-rotation features/configurations may be used and are contemplated such as, but not limited to, threads. The formation(s) may also aid in fixing bone screw angulation and/or orientation.

Figure 7:
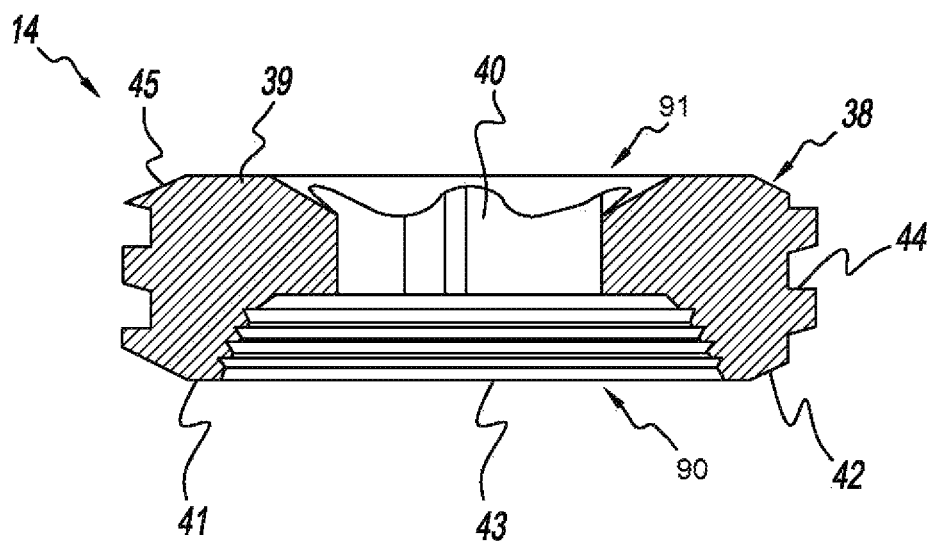
FIG. 7 is an enlarged sectional view of the setscrew of the present lateral spine plate implant.

Referring now to FIG. 7, a setscrew 14 is shown in sectional. Each setscrew 14 is preferably, but not necessarily, identical, and is characterized by a generally cylindrical body 38 with a generally flat upper or top surface 39 and a generally flat lower or bottom surface 41. The outer circumferential surface of the body 38 has external threads/threading 44 configured to mate with the internal threads/threading 22, 24 of the bone screw pockets 18, 20. The peripheral edge 45 of the upper surface 39 is preferably, but not necessarily, downwardly angled, slanted, or beveled. In like manner, the peripheral edge 42 of the lower surface is preferably, but not necessarily, upwardly angled, slanted or beveled.

The setscrew body 38 further has a bore 40 that extends axially through the body 38 from the upper surface 39 to the lower surface 41 and thus defines an upper opening 91 and a lower opening 90, the lower opening 90 configured as a rounded, spherical, or dome-shaped pocket in a complementary manner to the dome/spherical shape of the bone screw head 30. The pocket 90 has threads, serrations, or otherwise 43 about its inner circumference and along its axial length. The threads, serrations or otherwise 43 of the pocket 90 and the serrations/knurling/threads/helical cutout configuration(s) of the bone screw head 30 engage one another to seize, bind or capture the bone screw head 30 in order to fix the position/orientation of the bone screw 13 when the setscrew 14 is received into the bone screw pocket of the plate 12 and compresses against the bone screw head 30.

Figure 3:
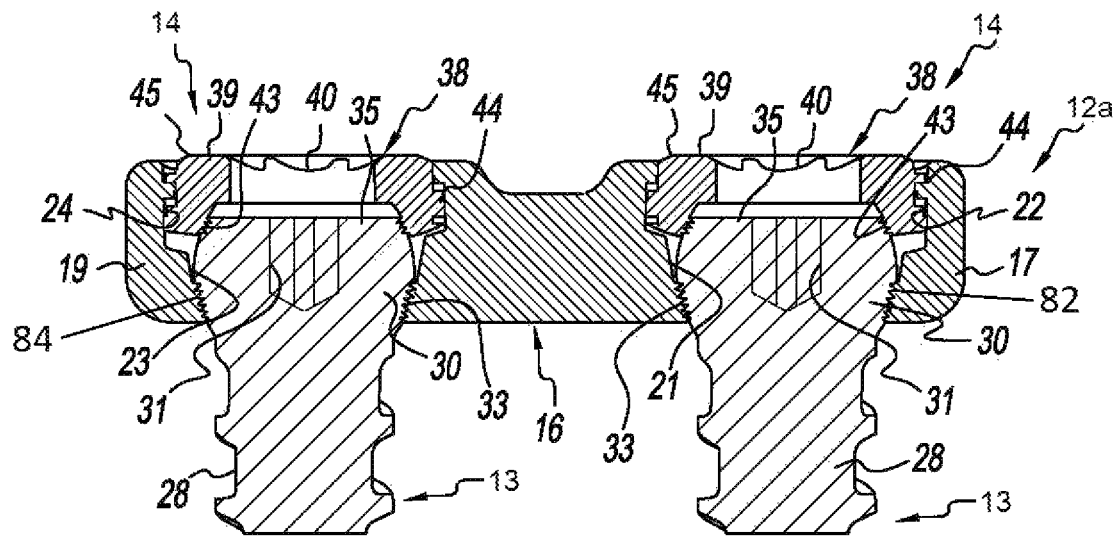
FIG. 3 is an enlarged, side sectional view of the assembled lateral spine plate implant of FIG. 1 with only the upper portion of the bone screws shown.

FIG. 3 shows an assembled spine plate implant 10 with the two bone screws 13 and the two setscrews 14 received in the bone screw pockets 21, 23 of the bone screw bores 18, 20 of the respective bosses 17, 19 of the plate 12a. The setscrews 14 have compressed against the bone screw heads 30 fixing their position/orientation relative to the spine plate 12. In FIG. 3, the bone screws are shown fixed into a transverse or 90 degree position/orientation relative to the spine plate 12a. Of course, the bone screws 30 may be fixed into other positions/orientations as necessary. Other spine plates 12 may be used.

It should be appreciated that dimensions of the formations, structures, and/or features of the present lateral spine plate implant and/or its components may be altered as desired within the scope of the present disclosure.

What is claimed is:

1. A lateral spine plate implant comprising:
a plate, wherein the plate comprises a thickness, an upper surface, a lower surface, a plurality of bores separated by a span, and a threaded bore between the plurality of bores in the span and offset from a centerline of the plate, wherein the threaded bore includes a rim extending around a portion of a circumference of the threaded bore, and wherein the threaded bore configured to receive an implantation tool, wherein each of the plurality of bores comprising:
an upper portion extending a first distance into the thickness from the upper surface and having a right cylinder configuration and interior threads around an inner circumference;
a lower portion having a spherical configuration defining an interior seating surface; and
a plurality of bone screws, wherein each of the plurality of bone screws comprises a head and a threaded shank extending from the head, the head having a spherical configuration with a textured exterior surface; and
a plurality of setscrews, wherein each of the plurality of setscrews comprises:
a generally cylindrical body having a bottom surface and a pocket extending into the body from the bottom surface, the pocket having an interior surface;
exterior threads around an outer circumference of the cylindrical body;
wherein orientation and angulation of each bone screw of the plurality of bone screws is fixed during installation by:
the exterior threads on a setscrew of the plurality of setscrews threadably engaging the interior threads on the plate;
the interior surface of the setscrew directly engaging the textured exterior surface of the head of a bone screw of the plurality of bone screws; and
the exterior surface of the head of the bone screw directly engaging the interior seating surface in the plate.

2. The lateral spine plate implant of claim 1, wherein each setscrew of the plurality of setscrews provides compression to the head of each of the respective bone screws of the plurality of bone screws so the interior surface of each of the setscrews engage the textured exterior surface of the head of each of the bone screws and the textured exterior surface of the head of each of the bone screws engage the interior seating surface in the plate.

3. The lateral spine plate implant of claim 2, wherein the engagement between each setscrew of the plurality of setscrews and the respective head of each of the bone screws of the plurality of bone screws, and the engagement between each head of the bone screws of the plurality of bone screws and the plate are configured to inhibit rotation of the bone screw relative to the plate.

4. The lateral spine plate implant of claim 1, wherein each setscrew of the plurality of setscrews further comprises a top surface and a socket extending into the body from the top surface and in communication with the pocket to form a bore that extends axially though the body from top surface to the bottom surface.

5. The lateral spine plate implant of claim 4, wherein the socket is configured to receive a setscrew installation tool.

6. The lateral spine plate implant of claim 1, wherein a peripheral edge of the bottom surface of each setscrew of the plurality of setscrews is angled.

7. The lateral spine plate implant of claim 6, wherein a peripheral edge of the top surface of each setscrew of the plurality of setscrews is angled.

8. An implant for attachment to lateral sides of adjacent vertebrae of a spine, the implant comprising:
a spine plate comprising:
a base;
a first boss extending from a first end of the base;
a first bore extending through the first boss and the base, the first bore comprising an upper portion and a lower portion, the upper portion having first internal threads, the lower portion having an annular, radially inwardly angled sidewall providing a first seat, the first seat having a first seating surface, the first bore having a first rim extending from an upper surface of the base and around a circumference of the first bore;
a second boss extending from a second end of the base and spaced apart from the first boss;
a second bore extending through the second boss and the base, the second bore comprising an upper portion and a lower portion, the upper portion of the second bore having second internal threads, and the lower portion of the second bore having an annular, radially inwardly angled sidewall providing a second seat, the second seat having a second seating surface, the second bore having a second rim extending from the upper surface of the base and around a circumference of the second bore; and
a threaded bore between the first bore and the second bore, where the threaded bore is offset from a centerline of the spine plate, and the threaded bore configured to receive an implantation tool;

a first bone screw having a first head and a first threaded shank extending from the first head, the first head having a first textured exterior;

a second bone screw having a second head and a second threaded shank extending from the second head, the second head having a second textured exterior surface;

a first setscrew comprising:
  a body having a top surface, a bottom surface, a socket extending into the body from the top surface, and a pocket extending into the body from the bottom surface, the pocket having a first inner surface;
  first exterior threads around an outer circumference of the body;

a second setscrew comprising:
  a body having a top surface, a bottom surface, a socket extending into the body of the second setscrew from the top surface of the second setscrew, and a pocket extending into the body of the second setscrew from the bottom surface of the second setscrew, the pocket of the second setscrew having a second interior surface;
  second exterior threads around an outer circumference of the body of the second setscrew;

wherein an orientation and angulation of the first bone screw is fixed during installation by:
  the first head of the first bone screw seated in the first bore so that the first threaded shank extends from the plate;
  the first exterior threads on the first setscrew threadably engaging the first internal threads on the plate to compress the first head of the first bone screw against the first seat;
  the first inner surface of the first setscrew directly engaging the first textured exterior surface of the first head of the first bone screw;
  the first textured exterior surface of the first head of the first bone screw directly engaging the first seating surface on the plate;

wherein an orientation and angulation of the second bone screw is fixed during installation by:
  the second head of the second bone screw seated in the second bore so that the second threaded shank extends from the plate;
  the second exterior threads on the second setscrew threadably engaging the second internal threads on the plate to compress the second head of the second bone screw against the second seat;
  the second interior surface of the second setscrew directly engaging the second textured exterior surface of the second head of the second bone screw;
  the second textured exterior surface of the second head of the second bone screw directly engaging the second seating surface on the plate.

9. The implant of claim 8, wherein the engagement between the first and second setscrews and the respective first and second heads of the first and second bone screws and the engagement between the first and second heads of the first and second bone screws and the plate are configured to inhibit rotation of the first and second bone screws relative to the plate.

10. The implant of claim 8, wherein a peripheral edge of the bottom surface of both the first setscrew and the second setscrew is angled.

11. The implant of claim 10, wherein a peripheral edge of the top surfaces of both the first setscrew and the second setscrew is angled.

12. The implant of claim 8, wherein the socket in the first setscrew is in communication with the pocket in the first setscrew, and the socket in the second setscrew is in communication with the pocket in the second setscrew.

13. The implant of claim 8, wherein the pocket of the first setscrew has an upper ledge for engaging a generally planar upper surface of the first bone screw when the first bone screw is received in the first seat of the first bore of the spine plate.

14. The implant of claim 13, wherein the pocket of the second setscrew has an upper ledge for engaging a generally planar upper surface of the second bone screw when the second bone screw is received in the second seat of the second bore of the spine plate.

15. The implant of claim 8, wherein the socket is configured to receive a setscrew installation tool.

* * * * *